United States Patent [19]

Qian et al.

[11] Patent Number: 5,430,054

[45] Date of Patent: Jul. 4, 1995

[54] PREPARATION METHODS OF DITERPENE LACTONE COMPOUNDS AND APPLICATION OF THE SAME TO ANTIFERTILITY

[75] Inventors: Shoa-Zhen Qian; Jia-Run Zheng; Xie-Yu Lu; Peng-Cheng Ma; Chong-Pu Zhang; Yun Chen; Ke-Xian Gu; Wen-Yan Xu; Zheng-Xing Zhang; Long-Sheng Sheng; Deng-Kui An; Ye Xu, all of Nanjing; Qi-Tai Zhen, Beijing, all of China

[73] Assignees: Jiangsu Family Planning Institute; China Pharmaceutical University; Institute of Dermatology, Chinese Academy of Medical Sciences, all of China

[21] Appl. No.: 629,411

[22] Filed: Dec. 18, 1990

[30] Foreign Application Priority Data

Dec. 22, 1989 [CN] China .............. 89 1 05432.4
Dec. 22, 1989 [CN] China .............. 89 1 05433.2
Dec. 22, 1989 [CN] China .............. 89 1 05434.0
Oct. 13, 1990 [CN] China .............. 90 1 05750.9

[51] Int. Cl.⁶ .............. A61K 31/34; C07D 307/77
[52] U.S. Cl. .............. 514/468; 514/841; 549/297
[58] Field of Search .............. 549/297; 514/468, 841

[56] References Cited

PUBLICATIONS

Shao–Zhen Qian et al., *Contraception* 33(2):105–110 (Feb. 1986).
Shao Zhen Qian et al., *Contraception* 36(3):335–345 (Sep. 1987).
Deng Fu–Xiao et al., *Acta Botanica Sinica* 27:316–519 (1985) [English translation of paragraphs related to triptolidenol].
S. Morris Kupchan et al., *J. Amer. Chem. Soc.* 94:20, pp. 7194–7195 (Oct. 1972).

*Primary Examiner*—Alan L. Rotman
*Assistant Examiner*—A. A. Owens
*Attorney, Agent, or Firm*—Merchant, Gould, Smith, Edell, Welter & Schmidt

[57] ABSTRACT

The invention provides methods of preparing a male antifertility agent composed of a diterpene lactone compound obtained from plants of the genus Tripterygium, the diterpene lactone compounds obtained from that method, and the use of the compounds as an antifertility agent.

19 Claims, No Drawings

PREPARATION METHODS OF DITERPENE LACTONE COMPOUNDS AND APPLICATION OF THE SAME TO ANTIFERTILITY

BACKGROUND OF INVENTION

This invention relates to the preparation methods of diterpene lactone compounds, especially methods of isolating the lactone compounds of antifertility from Tripterygium genus plants, and the compounds obtained, as well as use of said products of obtain male antifertility effects.

For the time being, there is not a single male antifertility agent that can be safely used in humans. We noted that Tripterygium Wilfordii Hook. f., a perennial twining wine of the family Celastraceae, as well as a number of lactone compounds isolated from the plant, including those in the form of Multiglycosidorom Tripterygii, possessed a definite male antifertility effect, besides their obvious effects of anti-inflammation and immunosuppression. The structures and preparation methods of Triptolidenol and Triptonide can be found in "Zhi Wu Xue Bao" (1985(27)) and "The Journal of American Chemical Society" (1972,94(20(7194). But their preparation methods are all complicated and the yields are low.

OBJECTS OF INVENTION

The main object of this invention is to provide an uncomplicated method of isolating the compounds of antifertility from Tripterygium Wilfordii Hook f. and/or Multiglycosidorom Tripterygii.

Another object of this invention is to provide diterpene lactone compounds which can be used as male antifertility agents.

A third object of the invention is to provide use of diterpene lactone compounds to obtain male antifertility effects.

SUMMARY OF THE INVENTION

This invention provides methods of preparing a male antifertility agent composed of a diterpene lactone compound, using Tripterygium genus plants as raw materials. The antifertility agents are prepared by boiling the raw plant materials in water, discarding the dregs, extracting the desired components from the boiled water, or directly from the raw materials, with organic solvents (the extractives may be distributed in two-phase solvents), then isolating the solution extracted and/or extractives or solutes eluted by chromatography, eluting with organic solvents or component organic solvents, collecting the diterpene lactone compounds, and then concentrating and crystallizing the desired components. The above-mentioned chromatography and crystallization steps can be repeated, in order to obtain pure products.

DESCRIPTION OF INVENTION

To realize the above objects, Tripterygium Wilfordii Hook f. (leaves, roots, barks or stalks) or Multiglycosidorom Tripterygii were chosen as raw materials. The process method comprises i) boiling Tripterygium Wilfordii Hook f. in water, discarding the dregs, extracting the desired products from the boiled water with organic solvents or component organic solvents, and concentrating the solution extracted, or ii) extracting the desired products from Tripterygium Wilfordii Hook f. or Multiglycosidorom directly with organic solvents, ethyl alcohol or chloroform (the extractives may be distributed in a two-phase solvent). After said step, the afore-mentioned concentrated solution of extract phase and/or extractives or solutes eluted are isolated by chromatography, and the desired products are eluted with organic solvents or compenent organic solvents. Depending upon the different organic solvents used, different diterpene lactone compounds are collected, concentrated and crystallized.

The above-mentioned steps of chromatography and crystallization may be carried out twice or more, in order to obtain pure products.

Organic or component organic solvents, suitable for the purpose, are listed iin Table 1 (the mark indicates feasible combinations).

TABLE 1

| Feasible Combinations | Chloroform | Methyl Alcohol | Ethyl Alcohol | Acetone | Benzene | Cyclohexane | Petroleum ether | Ethyl Ether | Ethyl Acetate |
|---|---|---|---|---|---|---|---|---|---|
| Chloroform | | | | | | | | | |
| Methyl Alcohol | | | | | | | | | |
| Ethyl Alcohol | | | | | | | | | |
| Acetone | | | | | | | | | |
| Benzene | | | | | | | | | |
| Cyclo-hexane | | | | | | | | | |
| Petroleum ether | | | | | | | | | |
| Ethyl Ether | | | | | | | | | |
| Ethyl acetate | | | | | | | | | |

The chromatographic columns used can be of silica gel or neutral alumina.

The chemical structures of the diterpene lactone compounds obtained according to the methods of this invention can be expressed as the following formula:

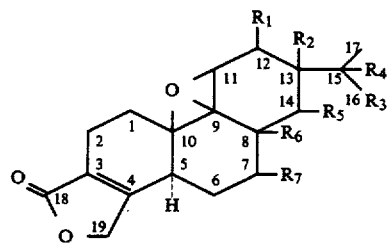

and when

1) $R_1$=—Cl, $R_2$=OH, $R_3$=CH$_3$, $R_4$=H, $R_5$=OH, $R_6$,$R_7$=—O—, the compound is Tripchloride;

2) $R_1$=—Cl, $R_2$=OH, $R_3$=CH$_2$OH, $R_4$=—H, $R_5$=OH, $R_6$,$R_7$=—O—, the compound is Chlorotriptolide;

3) $R_1$=—Cl, $R_2$=OH, $R_3$=CH$_2$OH, $R_4$=—H, $R_5$=OH, $R_6$=OH, $R_7$=—Cl, the compound is Dichlorotriptolide;

4) $R_1$=—Cl, $R_2$=OH, $R_3$=COOH, $R_4$=H, $R_5$=OH, $R_6,R_7$=—O—, the compound is Triptoditerpenic Acid B;

5) $R_1,R_2$=—O—, $R_3$=COOH, $R_4$=H, $R_5$=OH, $R_6,R_7$=—O—, the compound is Triptoditerpenic Acid A;

6) $R_1,R_2$=—O—, $R_3$=CH$_2$OH, $R_4$=H, $R_5$=OH, $R_6,R_7$=—O—, the compound is 16-Hydroxytriptolide;

7) $R_1,R_2$=—O—, $R_3$=CH$_3$, $R_4$=OH, $R_5$=OH, $R_6,R_7$=—O—, the compound is Triptolidenol;

8) $R_1,R_2$=—O—, $R_3$=CH$_3$, $R_4$=H, $R_5$= =O, $R_6,R_7$=—O—, the compound is Triptonide.

The raw material used in the above-mentioned methods may also be *Tripterygium Hypoglaueum (L'evl) Hutch* and/or *Tripterygium Regelii Sprague et Takada*, or all of Tripterygium genus.

When used as antifertility agents, the diterpene lactone compounds obtained by the above-mentioned methods have definite male antifertility effects, without any obvious cytotoxicity or other side effects, and, therefore, show considerably good prospects of usage. Moreover, the methods according to this invention are of high yields and are easy to put into effect.

DESCRIPTION OF PREFERRED EMBODIMENTS

The first aspect of this invention relates to the preparation method of Tripchlorolide.

*Multiglycosidorom Tripterygii* or the ethyl alcohol extract of *Tripterygium Wilfordii Hook. F.* is dissolved in an organic solvent (such as chloroform, ethyl alcohol, etc.), which is then isolated by chromatography, eluted with organic or component organic solvents (such as chloroform, ethyl alcohol, ethyl alcohol-chloroform, acetone-chloroform, cyclohexane-acetone, etc.), and further examined by TCL technique; and the eluate component containing Tripchloride is collected, merged and crystallized. In this manner, Tripchloride is obtained as a compound.

The above-mentioned column chromatography and crystallization processes can be carried out twice or more, to enhance the product's purity.

The chemical structure of Tripchlorolide obtained is:

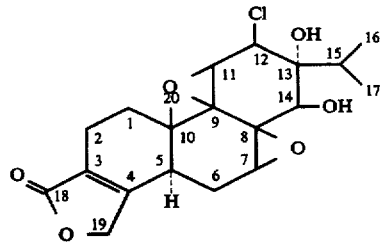

This structure can be verified by the following experimental results:

MS m/z(%): 396 (M+,0.88), 378(0.42), 361(1.88), 343(34.91), 273(17.06), 247(39.04), 229(17.33), 149(26), 121(23), 105(32), 71(100)

IR $\gamma$KBr cm$^{-1}$ 3530(Hydroxy group), 1751, 1673 ($\alpha$, $\beta$-unsaturated $\gamma$-lactone)

UV $\lambda_{max}^{MeOH}$217.8 nm

HNMR (400 MC, CDCl$_3$) $\delta$ ppm: 0.89 (3H, d, J=6.97 Hz, 16-H$_3$); 1.00 (3H, d, J=6.60 Hz, 17-H$_3$); 1.12 (3H, S, 20-H$_3$); 1.27, 1.61 (2H, 1-H$_2$); 1.98 (1H, t, 6$\beta$-H); 2.17, 2.32 (2H, 2-H$_2$); 2.20 (1H, m 6$\alpha$-H); 2.56 (1H, sept, 15-H); 2.75 (1H, d(d) 5-H); 3.12 (1H, d, J$_{14,12}$=1.46 Hz, 14-H); 3.45 (1H, d, J$_{7,6d}$=5.86 Hz, 7-H); 3.90 (1H, d, J=5.13 Hz, 11-H); 4.26 (1H, (d), J$_{12,11}$=5.13 Hz, J$_{12,14}$=1.46 Hz, 12-H); 4.74 (2H, m, 19-H$_2$)

$^{13}$CNMR (400 MC, DMSO-d$_6$) $\delta$ ppm: 13.27 (q, C$_{20}$); 15.17 (q, C$_{16}$); 15.38 (q, C$_{17}$); 17.01 (t, C$_2$); 23.26 (t, C$_6$); 28.98 (d, C$_{15}$); 30.41 (t, C$_1$); 35.74 (s, C$_{10}$); 39.88 (d, C$_5$); 57.66 (d, C$_{11}$); 59.08 (d, C$_{12}$); 61.31 (d, C$_7$); 70.47 (t, C$_{19}$); 76.24 (d, C$_{14}$); 125.27 (s, C$_3$); 161.20 (s, C$_4$); 174.19 (s, C$_{18}$); 60.51, 70.02, 76.58 (C$_8$,C$_9$,C$_{13}$).

The structure can also be verified by the X-ray monocrystal diffraction method.

Tripchloride is of colorless needle-like crystal with its melting point of 256°–258° C., showing purplish red in Kedde's reaction, easily dissolvable in 10% ethyl alcohol chloroform, dissolvable in methyl alcohol, ethyl alcohol and chloroform, and not dissolvable in water.

Tripchloride obtained from the above method has definite and reversible male antifertility effects without any cytotoxicity side effects.

The following results illustrate the effect of male antifertility of Tripchloride:

1. Primary Screening

Healthy male mice were selected of Kun Ming species, weighing 28.3±0.8 grams, with ten in each group. Medicine was poured down the throat of the mice at dosages of 0.3, 0.15 and 0.075 mg/kg per day for 32 consecutive days. These were merged with normal mature female mice at 1:1 ratio at the 26th day, and dissected at the 33th day. Then, one spermaductus was taken at full length, and the sperm was washed into a tube with 0.5 ml physiological saline. Then, the activity of the spermatozoa was observed and their relative number counted on a leucocytes counter plate. The testicle was excised and weighed, with the epididymis as pathological specimen. The female mice were dissected and their embryos (living and absorbed) were observed and counted on the 8th day after being merged. The testicle and epididymis were pathologically examined. Such were fixed by Bouin fluid, paraffin embedding, dyed with PAS threolignin, and examined under optical microscope; and then the germ cells were calculated by means of semiquantitative estimation based upon an improved Dym method, the normal percentages of spermatogenic cells for every period in the testic convoluted tubules were figured out for each experimental group and contrast group. The results are shown in Table 2, where 0 denotes the contrast value, 1, 2 and 3 refer to 60–90%, 30–60% and less than 30% of the contrast value, respectively. The results indicate: Tripchloride causes testicles to lose weight, resulting in apparently less number of spermatozoa and a lower activity of the same. As shown in Table 2, the dosages adopted are quantitatively related to the results, and administration of medicine leads to sterility. Moreover, the computed results for all the germ cells show abnormalities to different degrees, against the contrast group (see Table 3).

2. Rescreening:

Tripchloride was poured down the throat of male matured SD rats at a dosage of 0.05 mg/kg per day (six times a week). After 6–7 weeks, all were found sterile through mating experiments, with apparently decrease of density and percentage of living spermatozoa in the tails of epididymis (see Table 4). This dosage showed no obvious effects on their body weights, sex behaviors, serum testosterone and the weights of various accessory sex glands. Histological studies on testicles indicated that there were not any apparent changes except some fallen spermatoblasts and a slight disorder of epithelium arrangment in a few tubulus, and that the epithelium of epididymis was normal and a medium quantity of fallen metamorphosis spermatoblasts were observed in the tubulus.

TABLE 2

Effect of Tripchlorolide on the Germ Cells of Mice ($\bar{X} \pm SE$)

| Group (mg/kg) | Testicles's Weight (mg/100 g) | Sperm Activity (%) | | Total Number of Spermatozoa ($10^4$/per spermatoductus) | Number of Embryos | |
|---|---|---|---|---|---|---|
| | | Spermatozoid | Spermatium | | Living | Absorb. |
| 0.3 | 145.8 ± 6.8 | 5.7 ± 3.1 | 94.3 ± 3.0 | 3.0 ± 1.4 | 0 | 0 |
| 0.15 | 273.3 ± 33.9 | 24.1 ± 6.5 | 75.9 ± 6.1 | 3.7 ± 1.1 | 0 | 0 |
| 0.075 | 392.2 ± 55.1 | 34.8 ± 5.6 | 65.2 ± 5.3 | 13.4 ± 3.7 | 0 | 0 |
| Contrast | 660.1 ± 33.8 | 60.9 ± 2.0 | 19.1 ± 2.0 | 439.9 ± 86.4 | 8.7 ± 2.3 | 0.39 ± 0.33 |

TABLE 3

Effect of Tripchlorolide on the Germ Cells of Mice ($\bar{X} \pm SE$)

| Group (mg/kg) | Types of Germ Cells | | | | |
|---|---|---|---|---|---|
| | Spermatogonia | Spermatocyte | Spermatoblast | | Total |
| | | | 1–8 Period | 9–19 Period | |
| 0.3 | 2.8 ± 0.2 | 3 ± 0 | 3 ± 0 | 3 ± 0 | 11.3 ± 0.1 |
| 0.15 | 1.9 ± 0.2 | 2.2 ± 0.3 | 2.2 ± 0.3 | 2.4 ± 0.3 | 3.6 ± 0.1 |
| 0.075 | 0.6 ± 0.2 | 1.3 ± 0.4 | 1.2 ± 0.4 | 1.6 ± 0.4 | 4.7 ± 0.2 |
| Contrast | 0 | 0 | 0 | 0 | 0 |

TABLE 4

Effects of Tripchlorolide on the Reproduction of Rats ($\bar{X} \pm S.D.$)

| Group (n) | Spermatozoa in the tail of Epididymis | | Percentage of Pregnant | Mated Female Rats (Per Pregnant Embryo) | |
|---|---|---|---|---|---|
| | Density ($10^6$/ml) | Percentage of Living (%) | | Living | Dead |
| Contrast (10) | 104 ± 2.2 | 84 ± 3 | 10/10 | 12.6 ± 2.6 | 0 |
| Experiment (10) | 14 ± 6* | 6.5 ± 5.3* | 0/10* | 0 | 0 |

$P < 0.001$, as compared with the contrast group.

Histological studies on the viscera such as heart, liver, spleen, stomach, lung and kidney, etc., showed results of normality. The contrast group showed normal results in all the above aspects, as well. The experiment was carried out in two batches, with twnety rats in each (half of which were administered medicine and the other half not). Both batches showed similar results. It was also noted that Tripchloride has not any obvious effect on the incidence of perilymphocyte micronucleus of the rats.

As a male antifertility agent, Tripchloride can be administered orally, or injected, or applied to the skin, or administered through mucous membranes to obtain a male antifertility effect.

The second aspect of this invention relates to the preparation method of 16-Hydroxytriptolide and its analogues Triptoditerpenic Acid A, Triptoditerpenic Acid B, Chlorotriptolide and Dichlorotriptolide.

The process method in the 2nd aspect comprises boiling *Triopterygium Wilfordii Hook. f.* (leaves, velamens, roots or stalks, but preferably leaves) in water, descarding the dregs, extracting the desired components from the boiled water with organic solvents or component organic solvents, or extracting the desired components directly with ethyl alcohol, isolating the above-mentioned solution extracted by chromatography, and then eluting the desired components with organic solvents or component organic solvents, and collecting the eluate components which contain 16-Hydroxytriptolide, Triptoditerpenic Acid A, Triptoditerpenic Acid B, Chlorotriptolide and Dichlorotriptolide. After concentration, the compounds collected are crystallized, respectively, and the desired components of 16-Hydroxytriptolide, Triptoditerpenic Acid A, Triptoditerpenic Acid B, Chlorotriptolide and Dichlorotriptolide are obtained, respectively.

The above-mentioned organic or component organic solvents mainly refer to chloroform, methyl alcohol, methyl alcohol-benzene, ethyl acetate-petroleum ether, ethyl alcohol-chloroform, methyl alcohol-chloroform, acetone chloroform cyclohexane-acetone, acetone-bezene, etc..

The chromatographic column may be of silica gel or neutral alumina.

The chemical structure of the obtained 16-Hydroxytriptolide is:

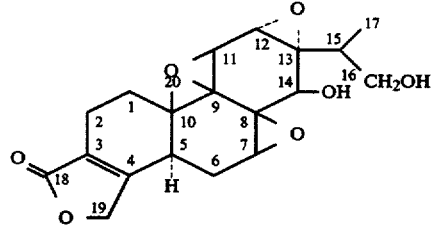

This chemical structure is verified by the following experimental results:

mp. 232°–233.5° C.

MS m/z (%) 376 (M+, 0.90), 358 (2.71). 345(1.38), 317 (7.79), 311(9.14), 271(21.59), 151(57.92), 43(75.00), 41(100.00), 31(63.77)

C—NMR 12.37(q, $C_{17}$), 13.64(q, $C_{20}$), 16.55(t, $C_2$)22.60(t, $C_6$), 28.96(t, $C_1$), 35.17(s, $C_{10}$), 35.72(d, $C_{15}$), 39.93(d, $C_5$), 54.46(d, $C_{12}$), 55.23(d, $C_{11}$), 59.70(d, $C_7$), 60.73(s), 61.59(t, $C_{16}$), 62.90(s), 64.34(s), 70.12(t, $C_{19}$), 71.56(d, $C_{14}$), 123.02(s, $C_3$), 162.32(s, $C_4$), 173.05(s, $C_{18}$)

$^1$H-NMR 0.84(3H, d, $C_{17}$—$H_3$), 0.96(3H, s, $C_{20}$—$H_3$), 1.30(2H, m, $C_1$—$H_2$), 1.97, 2.10 (2H, m, $C_2$—$H_2$), 1.82, 2.18 (2H, m, $C_8$—$H_2$), 2.11 (1H, m, $C_{15}$—H), 2.59 (1H, m, $C_5$—H)3.15, 3.28(2H, m, $C_{16}$—$H_2$), 3.34(1H, s, $C_{14}$—H), 3.36 (1H, d, $C_7$—H), 3.65 (1H, d, $C_{12}$—H), 3.90 (1H, d, $C_{11}$—H), 4.60 (1H, $C_{14}$—OH), 4.81(2H, q, $C_{19}$—$H_2$)

This structure is also verified by the X-ray monocrystal diffration method.

The chemical structure of the obtained Triptoditerpenic Acid A, Triptoditerpenic Acid B, Chlorotriptolide and Dichlorotriptolide are expressed as follows:

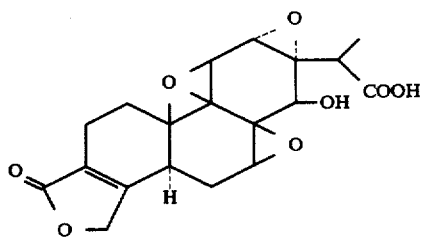

Triptoditerpenic Acid A

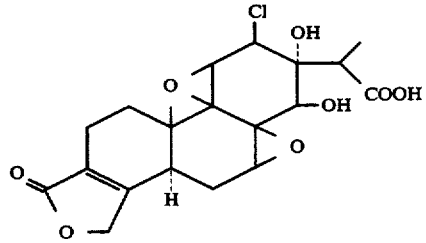

Triptoditerpenic Acid B

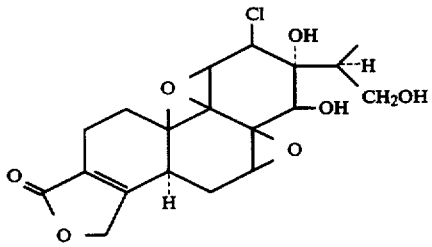

Chlorotriptolide

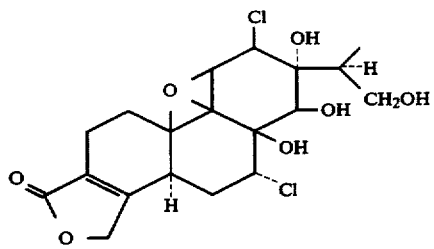

Dichlorotriptolide

Besides their definite effect of male antifertility, 16-Hydroxytriptolide, Triptoditerpenic Acid A, Triptoditerpenic Acid B, Chlorotriptolide and Dichlorotriptolide can also be used as anti-inflammatory or immunosuppression or anti-neoplastic drugs.

The third aspect of this invention relates to the preparation method of Triptolidenol. Velamens or other parts of Tripterygium Wilfordii Hook. f. are extracted with organic solvent, the extractives are distributed in a two-phase solvent, and the dissolved compounds are isolated by column chromatography, eluted with organic solvent, then the eluate component containing Triptolidenol is collected. A pure product of Triptolidenol is obtained through another column chromatography and recrystallization.

The above-mentioned organic or component organic solvents mainly refer to chlorofom, ether, cyclohexane-acetone, petroluem ether-acetone, acetone-benzene, methyl alcohol-chloroform, acetone-chloroform, ethyl alcohol-chloroform, ethyl acetate-chloroform, cyclohexane-chloroform, etc.

The chemical structure of the obtained Triptolidenol is:

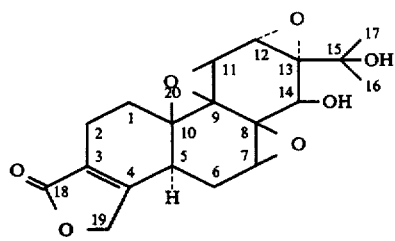

The compound has a definite male antifertility function. When the dosage is ¼ to ⅓ that for treating infectious arthritis, there are not any apparent side effects in clinical observations, nor any pathological changes under the optical and electronic microscopes in animal experiments.

The forth aspect of this invention relates to the preparation method of Triptonide. Tripterygium Wilfordii Hook. f. (roots, stalks or leaves) is extracted with ethyl alcohol, and the components extracted are isolated by column chromatography. As an alternative, Tripterygium Wilfordii Hook f. can be boiled in water, and the desired components dissolved in the water are extracted with chloroform, the extract is then concentrated and the desired components in the extract are isolated by column chromatography, eluted with organic solvents and the components containing Triptonide are collected, isolated by column chromatography once more, and then recrystallized, to obtain a pure product of Triptonide.

The above-mentioned organic or component organic solvents mainly refer to chloroform, methyl alcohol-chloroform, acetone-chloroform, ethyl acetate-chloroform, ethyl alcohol-chloroform, cyclohexane-chloroform, acetone-benzene, cyclohexane-acetone, ethyl ether and petroleum benzene-acetone, etc.

The chemical structure of the above-obtained Triptonide is:

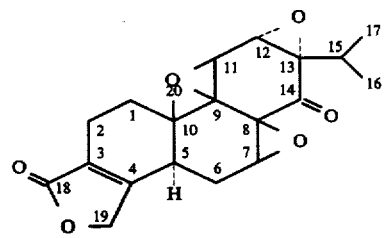

The following examples illustrate the invention in a detailed way.

EXAMPLE 1

100 grams of *Multiglycosidorom Tripterygii* are dissolved in chloroform to form a 50% chloroform solution, and the desired components are isolated through a silica gel chromatographic column (1000 g silica gel, wet packed with 10% ethyl alcohol chloroform), and gradiently eluted with ethyl alcohol-chloroform, examined by TLC technique, and the eluate components containing Tripchloride are collected and merged.

Further, 1 g of the above raw product containing Tripchloride is isolated by rotary thin layer chromatography, using cyclohexane-acetone as eluent. The eluate in test tubes Nos. 15 to 25 (15 ml per test tube) is collected with partial collectors, concentrated, and then recrystallized in chloroform twice, to obtain a pure product of Tripchloride.

Used for silica thin layer chromatography are: 97 portions of chloroform and 3 portions of ethyl alcohol; Kede's reagent is used as developer.

EXAMPLE 2

*Tripterygium Wilfordii Hook.f.* is boiled in water, and the dregs are discarded; the desired components in the boiled water are extracted with chloroform, and the extractives are further concentrated; and then carry on as stated in Example 1.

EXAMPLE 3

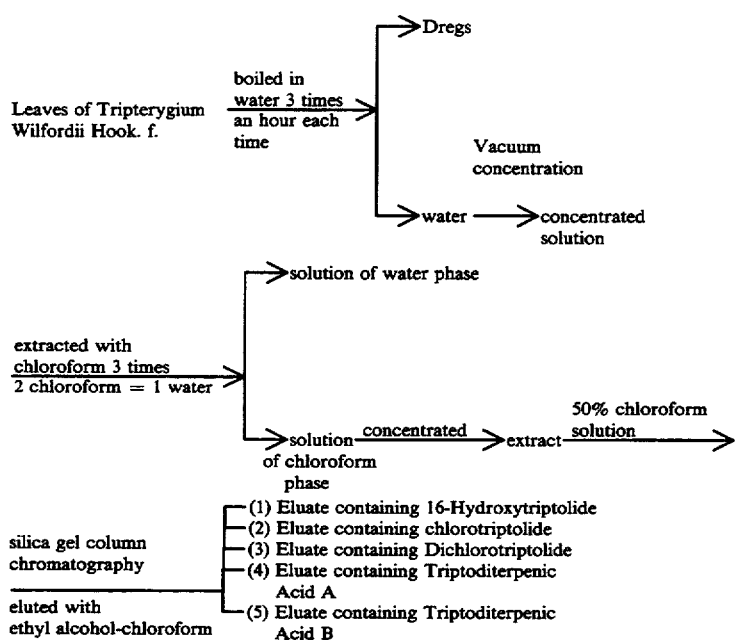

The eluates obtained under (1), (2), (3), (4), and (5) are concentrated and then fed through a low pressure silica gel chromatographic column ($N_2$, 1 kg/cm$^2$), eluted with cyclohexane-acetone, and the macrocrystallines of different components are obtained. The said macrocrystallines are recrystallized in chloroform, to obtain pure products of 16-Hydroxytriptolide, Triptoditerpenic Acid A, Triptoditerpenic Acid B, Chlorotriptolide and Dichlorotriptolide.

EXAMPLE 4

20 kg of leaves of *Tripterygium Wilfordii Hook. f.* are extracted with 75–95% ethyl alcohol. The solution of extractives is concentrated and then distributed in a solution of chloroform-water. The solute in chloroform is isolated through a chromatographic column, and gradiently eluted with 1–10% ethyl alcohol chloroform. The eluate components containing 16-Hydroxytriptolide, Triptoditerpenic Acid A, Triptoditerpenic Acid B, Chlorotriptolide and Dichlorotriptolide are collected and isolated through low pressure silica gel H chromatographic columns, and further eluted with cyclohexane-acetone; and these eluates containing 16-Hydroxytriptolide, Triptoditerpenic Acid A, Triptoditerpenic Acid B, Chlorotriptolide and Dichlorotriptolide are collected and merged, concentrated and crystallized, respectively. Pure products will be obtained after recrystallization in chloroform.

EXAMPLE 5

Velamens of *Tripterygium Wilfordii Hook. f.* are extracted with ethyl alcohol, the extractive is distributed in a solution of chloroform-water. The solute in chloroform is isolated through a silica gel chromatographic column, and eluted with ethyl alcohol-chloroform. The eluate components of the same lactone are collected and isolated through a silica gel chromatographic column twice. A pure product will be obtained after recrystallization in chloroform.

The above-mentioned chromatographic column may also be of neutral alumina and the solvents used in the processes of extraction, distribution and elution may also be other kinds of organic solvents, such as ethyl acetate-petroleum ether, methyl alcohol-chloroform, acetone-chloroform, cyclohexane-acetane or acetone-benzene, etc.

EXAMPLE 6

*Tripterygium Wilfordii Hook. f.* (roots, stalks, or leaves) is extracted with 70–95% ethyl alcohol. The solution of extractives is concentrated, and 100 g of the concentrated solution are isolated through a silica gel chromatographic column (1000 g silica gel, wet packed with 1% ethyl alcohol chloroform), eluted with 1% ethyl alcohol chloroform and the eluate alcohol component containing Triptonide is collected and merged.

The component containing Triptonide is isolated once more by column chromatography, further eluted with ethyl ether, and the eluate containing Triptonide is collected with 100 ml little bottles and merged. A pure product of Triptonide will be obtained after recrystallization in chloroform twice.

EXAMPLE 7

*Tripterygium Wilfordii Hook. f.* is boiled in water, the dregs are discarded, and the desired components in the boiled water are extracted with chloroform and the solution of extractives is concentrated. The successive processes of chromatography, elution, collection, rechromatography and elution and recrystallization are carried out according to the methods stated in Example 6.

The organic solvents used in column chromatography and elution may also be benzene-acetone, cyclohexane-acetone, ethyl ether-methyl alcohol and ethyl acetate-petroleum ether, etc.

What is claimed is:

1. A method of producing a purified diterpene lactone compound, comprising:
    (a) treating a plant part derived from a Tripterygium plant with an organic solvent to provide an extract containing the diterpene lactone compound; and
    (b) separating the diterpene lactone compound from other substances in the extract.

2. The method according to claim 1, wherein step (b) comprises separating the diterpene lactone compound from the other substances in the extract by gradient elution column chromatography using a second organic solvent.

3. The method according to claim 2, wherein the second organic solvent is selected from the group consisting of chloroform, methyl alcohol, ethyl alcohol, acetone, benzene, cyclohexane, petroleum ether, ethyl ether, ethyl acetate, and combinations thereof.

4. The method according to claim 3, further comprising: step (c) purifying the diterpene lactone compound.

5. The method according to claim 4, wherein step (c) comprises purifying the diterpene compound by chromatographic separation, crystallization, or a combination thereof.

6. The method according to claim 1, wherein prior to step (a), the plant part is boiled in water to provide an aqueous extract containing the diterpene lactone compound; and step (a) comprises treating the aqueous extract with the organic solvent.

7. The method according to claim 1, wherein the Tripterygium plant is *T. wilfordii Hook. f.* or *Multiglycosidorom tripterygii.*

8. The method according to claim 1, wherein the Tripterygium plant is *T. Regelii Sprague et Takada* or *T. Hypoglaucum (L'evl).*

9. The method according to claim 1, wherein the diterpene lactone compound has a chemical formula:

wherein
$R_1, R_2 = $ —Cl and —OH, or —O—;
$R_3 = CH_3$;
$R_4 = $ H or OH;
$R_5 = $ OH or =O; and
$R_6, R_7 = $ —O—;
and when
(a) $R_1 = $ —Cl and $R_2 = $ —OH: $R_4 = $ H and $R_5 = $ OH; and
(b) $R_1, R_2 = $ —O—: $R_4 = $ OH and $R_5 = $ OH; or $R_4 = $ H and $R_5 = $ O.

10. The method according to claim 9, wherein the diterpene lactone compound is selected from the group consisting of tripchlorolide, triptolidenol, triptonide, and combinations thereof.

11. The method according to claim 1, wherein the diterpene lactone compound has a chemical structure:

wherein
$R_1 = $ —Cl and $R_2 = $ —OH, or $R_1, R_2 = $ —O—;
$R_3 = CH_2OH$ or COOH;
$R_4 = $ H;
$R_5 = $ OH;
$R_6 = $ OH and $R_7 = $ —Cl, or $R_6, R_7 = $ —O—;
and when
(a) $R_1 = $ —Cl, $R_2 = $ —OH, $R_3 = CH_2OH$: $R_6 = $ OH, $R_7 = $ —Cl, or $R_6, R_7 = $ —O—;
(b) $R_1 = $ —Cl, $R_2 = $ —OH, $R_3 = $ COOH: $R_6, R_7 = $ —O—; and
(c) $R_1, R_2 = $ —O—, $R_3 = CH_2OH$ or COOH: $R_6, R_7 = $ —O—.

12. The method according to claim 11, wherein the diterpene lactone compound is selected from the group consisting of chlorotriptolide, dichlorotriptolide, triptoditerpenic acid B, triptoditerpenic acid A, 16-hydroxytriptolide, and combinations thereof.

13. A method for reducing fertility in a male animal, comprising:
    administering to the animal an effective amount of a composition containing a diterpene lactone compound derived from a Tripteryglum plant; the diterpene lactone compound having a chemical formula:

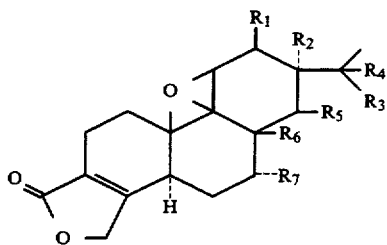

wherein
$R_1, R_2 = $ —Cl and —OH, or —O—;
$R_3 = CH_3$;
$R_4 = $ H or OH;
$R_5 = $ OH or =O; and
$R_6, R_7 = $ —O—;
and when
(a) $R_1 = $ —Cl and $R_2 = $ —OH: $R_4 = $ H and $R_5 = $ OH; and
(b) $R_1, R_2 = $ —O—: $R_4 = $ OH and $R_5 = $ OH; or $R_4 = $ H and $R_5 = $ O.

14. The method according to claim 13, wherein the diterpene lactone compound is selected from the group consisting of chlorotriptolide, dichlorotriptolide, triptoditerpenic acid B, triptoditerpenic acid A, 16-hydroxytriptolide, and combinations thereof.

15. The method according to claim 13, wherein the composition is administered orally, by injection, or by application to a mucous membrane.

16. A method for reducing fertility in a male animal, comprising:
   administering to the animal an effective amount of a composition containing a diterpene lactone compound prepared according to the process of:
   (a) treating a plant part derived from a Tripterygium plant with an organic solvent to provide an extract containing the diterpene lactone compound;
   (b) separating the diterpene lactone compound from other substances in the extract by chromatographic separation;
   (c) purifying the diterpene lactone compound; and
   (d) combining the purified diterpene lactone compound with a carrier to form the composition.

17. A diterpene lactone compound, produced by the method according to claim 1.

18. The diterpene lactone compound according to claim 17, selected from the group consisting of tripchlorolide, chlorotriptolide, dichlorotriptolide, triptodeterpenic Acid B, triptodeterpenic Acid A, 16-hydroxytriptolide, triptolidenol, and triptonide.

19. The diterpene lactone compound according to claim 17, selected from the group consisting of tripchlorolide, triptolidenol, and triptonide.

* * * * *

UNITED STATES PATENT AND TRADEMARK OFFICE
CERTIFICATE OF CORRECTION

PATENT NO. : 5,430,054
DATED : July 4, 1995
INVENTOR(S) : Qian, et al

It is certified that error appears in the above-indentified patent and that said Letters Patent is hereby corrected as shown below:

On the title page, under Inventor [75], "Shoa-Zhen Qian" should read -- Shao-Zhen Qian --.

Signed and Sealed this

Twelfth Day of November, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,430,054
DATED : July 4, 1995
INVENTOR(S) : Qian, et al

It is certified that error appears in the above-indentified patent and that said Letters Patent is hereby corrected as shown below:

At cols. 2-3 (bridging), Table 1 should read as follows:

Table 1

| Feasible Combinations | Chloroform | Methyl Alcohol | Ethyl Alcohol | Acetone | Benzene | Cyclohexane | Petroleum ether | Ethyl Ether | Ethyl acetate |
|---|---|---|---|---|---|---|---|---|---|
| Chloroform | ✓ | ✓ | ✓ | ✓ |   | ✓ |   |   | ✓ |
| Methyl Alcohol | ✓ | ✓ |   |   | ✓ |   |   | ✓ |   |
| Ethyl Alcohol | ✓ |   | ✓ |   |   |   |   |   |   |
| Acetone | ✓ |   |   |   | ✓ | ✓ | ✓ |   |   |
| Benzene |   | ✓ |   | ✓ |   |   |   |   |   |
| Cyclo-hexane | ✓ |   |   | ✓ |   |   |   |   |   |
| Petroleum ether |   |   |   | ✓ |   |   |   |   | ✓ |
| Ethyl Ether |   | ✓ |   |   |   |   |   | ✓ |   |
| Ethyl acetate | ✓ |   |   |   |   |   | ✓ |   | ✓ |